US012767619B2

(12) United States Patent
Paul et al.

(10) Patent No.: US 12,767,619 B2
(45) **Date of Patent: *Oct. 20, 2026**

(54) ENERGY-EFFICIENT PROCESS FOR SEPARATION OF 1-BUTENE FROM A HYDROCARBON STREAM WITH OPTIMIZED VAPOUR COMPRESSION

(71) Applicant: Evonik Oxeno GmbH & Co. KG, Marl (DE)

(72) Inventors: Niklas Paul, Marl (DE); Armin Matthias Rix, Marl (DE); Tanita Valèrie Six, Dortmund (DE); Tanja Steenweg, Dortmund (DE); Stephan Peitz, Oer-Erkenschwick (DE); Guido Stochniol, Haltern am See (DE); Vinzenz Fleischer, Marl (DE); Lea Wessner, Dortmund (DE); Moritz Schröder, Muenster (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 123 days.

This patent is subject to a terminal disclaimer.

(21) Appl. No.: 18/958,116

(22) Filed: Nov. 25, 2024

(65) Prior Publication Data

US 2025/0171385 A1 May 29, 2025

(30) Foreign Application Priority Data

Nov. 29, 2023 (EP) .................................... 23213040

(51) Int. Cl.
*C07C 7/04* (2006.01)
*C07C 7/00* (2006.01)

(52) U.S. Cl.
CPC ................ *C07C 7/04* (2013.01); *C07C 7/005* (2013.01)

(58) Field of Classification Search
None
See application file for complete search history.

(56) References Cited

U.S. PATENT DOCUMENTS

| | | | |
|---|---|---|---|
| 7,932,428 | B2 | 4/2011 | Rix et al. |
| 8,002,952 | B2 | 8/2011 | Sechrist |
| 10,774,020 | B2 | 9/2020 | Di Girolamo et al. |
| 11,952,340 | B2 | 4/2024 | Peitz et al. |
| 2007/0149839 | A1 | 6/2007 | Rix et al. |
| 2007/0203369 | A1 | 8/2007 | Praefke et al. |

(Continued)

FOREIGN PATENT DOCUMENTS

| | | |
|---|---|---|
| CN | 112358375 | 2/2021 |
| DE | 10 2005 062 700 | 7/2007 |

(Continued)

OTHER PUBLICATIONS

European Search Report received for European Patent Application No. 23213040.1, mailed on May 31, 2024, 8 pages.

(Continued)

*Primary Examiner* — Vishal V Vasisth
(74) *Attorney, Agent, or Firm* — Grüneberg Global IP, PLLC

(57) ABSTRACT

A process separates 1-butene from a hydrocarbon stream containing at least 1-butene, 2-butene, n-butane and isobutane in a separation unit having at least two distillation columns DK1 and DK2, wherein the heat of condensation is recirculated into the process by optimized vapour compression in order to save energy costs and $CO_2$ emissions.

20 Claims, 9 Drawing Sheets

(56) References Cited

U.S. PATENT DOCUMENTS

| | | | |
|---|---|---|---|
| 2017/0166497 | A1 | 6/2017 | Kim et al. |
| 2020/0207687 | A1 | 7/2020 | Kim et al. |
| 2021/0363075 | A1 | 11/2021 | Kim et al. |
| 2024/0059633 | A1 | 2/2024 | Lutze et al. |
| 2025/0171383 | A1 | 5/2025 | Paul et al. |
| 2025/0171384 | A1 | 5/2025 | Paul et al. |
| 2025/0171386 | A1 | 5/2025 | Paul et al. |

FOREIGN PATENT DOCUMENTS

| | | | |
|---|---|---|---|
| EP | 1 806 300 | | 7/2007 |
| EP | 1 813 588 | | 8/2007 |
| EP | 2 875 850 | A1 | 5/2015 |
| EP | 3 626 804 | A2 | 3/2020 |
| EP | 3 680 224 | | 7/2020 |
| EP | 3 626 804 | B1 | 2/2022 |

OTHER PUBLICATIONS

Paul et al., U.S. Appl. No. 18/957,961, filed Nov. 25, 2024.
Paul et al., U.S. Appl. No. 18/958,063, filed Nov. 25, 2024.
U.S. Appl. No. 18/957,961, filed Nov. 25, 2024, Paul et al.
U.S. Appl. No. 18/958,063, filed Nov. 25, 2024, Paul et al.
U.S. Office Action dated Jun. 29, 2026, in U.S. Appl. No. 18/958,063, 12 pages.
U.S. Office Action dated Jun. 26, 2026, in U.S. Appl. No. 18/957,961, 13, pages.

ENERGY-EFFICIENT PROCESS FOR SEPARATION OF 1-BUTENE FROM A HYDROCARBON STREAM WITH OPTIMIZED VAPOUR COMPRESSION

CROSS-REFERENCE TO RELATED APPLICATIONS

This patent application claims priority to European Patent Application No. 23213040.1, filed on Nov. 29, 2023, in the European Patent Office, the entire disclosure of which is hereby incorporated by reference herein.

BACKGROUND OF THE INVENTION

Field of the Invention

The present invention relates to a process for separating 1-butene from a hydrocarbon stream containing at least 1-butene, 2-butene, n-butane and isobutane in a separation unit comprising at least two distillation columns DK1 and DK2, wherein the heat of condensation is recirculated into the process by optimized vapour compression in order to save energy costs and $CO_2$ emissions.

1-Butene can be obtained in large amounts from technical C4 hydrocarbon streams, for example the C4 cut from steamcrackers or FCC units. These C4 hydrocarbon streams consist essentially of butadiene, the monoolefins isobutene, 1-butene and the two 2-butenes (cis- and trans-2-butene), and the saturated hydrocarbons isobutane and n-butane. Because of the small differences in the boiling points of the constituents, the low separation factors thereof and the formation of azeotropes, exclusively distillative workup of C4 hydrocarbon streams is difficult and uneconomic.

Typically, therefore, the butadiene is first separated off by extractive distillation or hydrogenated selectively to butenes. What remains in each case is a C4 hydrocarbon stream (called raffinate 1) containing not only the saturated hydrocarbons n-butane and isobutane but also the olefins isobutene, 1-butene and 2-butenes, while the butadiene is present in small amounts at most.

Since the boiling points of 1-butene and isobutene are close to one another, it is generally not possible to economically separate 1-butene from corresponding C4 hydrocarbon streams via simple distillation. The isobutene is therefore very substantially removed, for example by etherification with alcohols, e.g. methanol or ethanol to give MTBE or ETBE. The largely reactive removal of the isobutene gives rise to a C4 hydrocarbon stream (called raffinate 2) containing the linear butenes (1- and 2-butenes) and the saturated hydrocarbons isobutane and n-butane.

Description of Related Art

The separation of 1-butene from such C4 hydrocarbon streams is possible and is used in the chemical industry. The separation is effected in a distillation unit comprising at least two distillation columns. Isobutane and 1-butene are obtained at the top of the first distillation column and directed to the second distillation column. Then isobutane and 1-butene are separated from one another in the second distillation column. Such a process is disclosed, for example, in DE 10 2005 062 700 A1.

In the known processes, the energy needed for the separation of the C4 hydrocarbon stream is typically introduced into the bottom of the two distillation columns via heating steam. It is true that heating steam is generally available at chemical production sites. But, in the volumes needed for the separation tasks in question, the use of heating steam means a cost factor that cannot be underestimated. Furthermore, the generation of heating steam generates a large volume of $CO_2$.

SUMMARY OF THE INVENTION

It was therefore the object of the present invention to provide a process in which energy and $CO_2$ emissions can be saved by comparison with the known processes and which can be integrated into existing plants.

DETAILED DESCRIPTION OF THE INVENTION

Figure 1:
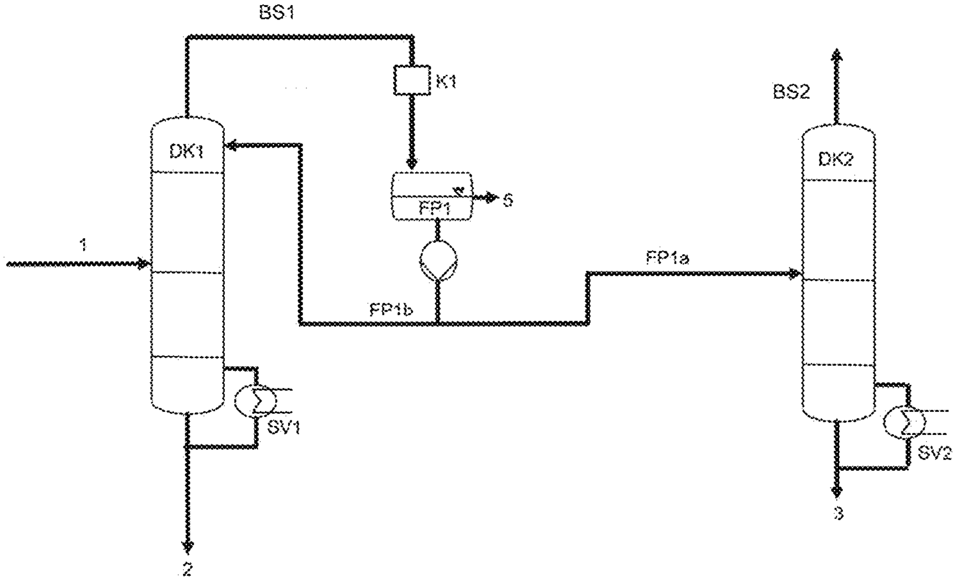
FIG. 1 shows a configuration according to a conventional dual pressure circuit without the thermal integration according to the invention.

This problem is solved by the embodiment of the process proposed in the description herein. Preferred embodiments are also specified in the dependent embodiments. The process according to the invention is a process for separating 1-butene from a raffinate 2 stream containing at least 1-butene, 2-butene, n-butane, isobutene and isobutane in a separation unit comprising at least two distillation columns DK1 and DK2, wherein

- the first distillation column DK1 has at least one reboiler SV1 and the second distillation column DK2 has at least one reboiler SV2;
- the reboiler SV1 is fed with a stream which is withdrawn at the lower end of DK1 and, after passing through the respective reboiler, is guided back to DK1;
- the reboiler SV2 is fed with a stream which is withdrawn at the lower end of DK2 and, after passing through the respective reboiler, is guided back to DK2; where the process comprises the following steps:

(a) the raffinate 2 stream is directed to the first distillation column DK1 and separated in DK1 into at least one vapour stream BS1 which comprises at least 1-butene and isobutane and is withdrawn at the top of DK1, and at least one bottom stream which comprises at least 1-butene, n-butane and 2-butene and is withdrawn at the bottom of DK1;

(b) at least a portion of vapour stream BS1 is compressed, giving rise to a compressed stream VB1 relative to vapour stream BS1;

(c) energy is transferred from the compressed stream VB1 to the stream in reboiler SV1;

(d) stream VB1 is directed at least partly to the second distillation column DK2 and separated in DK2 into at least one vapour stream BS2 which comprises at least isobutane and is withdrawn at the top of DK2, and at least one bottom stream which comprises at least 1-butene and is withdrawn at the bottom of DK2;

(e) the vapour stream BS2 is at least partly compressed, giving rise to a compressed stream VB2 relative to the vapour stream BS2; and (f) energy is transferred from the compressed stream VB2 to the stream in reboiler SV2.

One advantage of the process according to the invention is that the vapour streams BS1 and BS2 obtained in the two columns DK1 and DK2 are subjected to a compression, accordingly upgraded and exploited in reboilers SV1 and SV2, and energy is thus introduced into the respective bottoms. The result of the energy transfer in the reboilers SV1 and SV2 is that significantly less heating steam, if any at all, has to be used for heating of distillation columns DK1 and DK2. It is thus possible to achieve (almost) complete electrification of the energy-intensive process, which in turn enables the use of green power. This saves energy costs and $CO_2$ emissions.

According to the present invention, the starting stream from which the 1-butene is to be separated is a raffinate 2 stream containing at least 1-butene, 2-butene, n-butane and isobutane. Corresponding streams are available on the market, for example as a C4 cut from steamcrackers or FCC units. It has already been mentioned in the introduction that raffinate 2 is formed by removal of polyunsaturated C4 hydrocarbons, especially butadiene, and isobutene from the stream. Complete removal is not possible in many cases for economic and technical reasons. However, the amounts of polyunsaturated C4 hydrocarbons, especially butadiene, and isobutene should be at a minimum.

The raffinate 2 used preferably contains less than 2500 ppm, preferably less than 1000 ppm, more preferably less than 500 ppm, of isobutene. If higher amounts of isobutene are present in the starting stream, it would be possible for an MTBE or ETBE synthesis (methyl tert-butyl ether=MTBE/ethyl tert-butyl ether=ETBE) to be effected between the two distillation columns DK1 and DK2, in order to react the isobutene with methanol (to give MTBE) or ethanol (to give ETBE) and then to separate off the MTBE or ETBE (cf. EP 1 806 330 A1 or EP1 813 588 A1). It is thus possible to very greatly reduce the concentration of isobutene upstream of the second distillation column DK2. This is because isobutene would be obtained in the bottom in the second distillation column and hence in the 1-butene.

Further preferably, the raffinate 2 used in the process of the present invention contains less than 4% by weight of polyunsaturated C4 hydrocarbons. In a particularly preferred embodiment, the concentration of the polyunsaturated C4 hydrocarbons should be less than 500 ppm. If the streams should contain higher amounts of butadiene, it would be possible to conduct a selective hydrogenation beforehand, in which the butadiene is converted to butenes and/or butanes. Corresponding processes are known to the person skilled in the art, for example from EP 3 680 224 A1.

The raffinate 2 stream used may additionally contain certain amounts of water, especially in an amount of 150 to 4000 ppm. It is preferable that the water is at least partly separated off by the process described here. The water will accumulate in the respective vapour stream BS1 and BS2 in each of the two distillation columns DK1 and DK2 and be obtained as a second liquid phase after condensation, which can be separated off via udders in the distillate vessels of DK1 and/or DK2. The bottom products of DK1 and of DK2 feature very low contents of butadiene and water, preferably each below 100 ppm, more preferably below 5 ppm.

The process according to the invention is conducted in a separation unit comprising at least the two distillation columns DK1 and DK2. DK1 is the first distillation column and has at least one reboiler SV1. DK2 is the second distillation column and has at least one reboiler SV2. In a preferred embodiment, the distillation column has only one reboiler SV1. It is additionally preferable that the distillation column DK1 has only the one reboiler SV2. The pressures in the two distillation columns DK1 and DK2 should in particular be chosen such that the separation task is made easier by the influencing of relative volatility, but the compression of the volume flows BS1 and BS2 does not become too energy-intensive. The terms "first distillation column", "distillation column DK1" and "DK1" should be considered to be synonymous in the context of the present invention. The terms "second distillation column", "distillation column DK2" and "DK2" should likewise be considered to be synonymous in the context of the present invention.

The energy needed for the separation task is introduced into the first distillation column DK1 via the reboiler SV1. The reboiler SV1 is fed with a stream which is withdrawn at the lower end of DK1 and, after passing through the respective reboiler, is guided back to DK1. The stream is heated as it passes through the reboiler SV1.

The situation is comparable for the reboiler SV2 of the second distillation column DK2, by means of which energy needed for the separation task is introduced. For this purpose, the reboiler SV2 is fed with a stream which is withdrawn at the lower end of DK2 and, after passing through the respective reboiler, is guided back to DK2. The stream is heated as it passes through the reboiler SV2 and at least partly evaporates as it does so.

According to the invention, "reboilers" refer to evaporators that heat the bottom of the respective distillation column. Such a reboiler is typically disposed outside the respective distillation column. Since reboilers transfer energy, in particular heat, from one stream to another, they are heat transferrers. The stream to be evaporated is drawn off from the bottom of the distillation column via a draw and fed to the reboiler. The evaporated stream, with or without a residual proportion of liquid, is returned back to the respective distillation column in the region of the bottom via at least one feed.

Suitable evaporators that can be used as reboilers are, for example, natural circulation evaporators, forced circulation evaporators, forced circulation flash evaporators, kettle evaporators, falling-film evaporators or thin-film evaporators. Heat exchangers for the evaporator that are typically used in the case of natural circulation evaporators and forced circulation evaporators are a shell-and-tube or plate apparatus. As well as those mentioned, it is alternatively possible to use any other design of evaporator which is known to those skilled in the art and is suitable for use in a distillation column.

The raffinate 2 which is directed to the first distillation column DK1 is separated in distillation column DK1 into at least two streams, i.e. at least one vapour stream BS1 which comprises at least 1-butene and isobutane and is withdrawn at the top of DK1, and at least one bottom stream which comprises at least 1-butene and 2-butene and is withdrawn at the bottom of DK1. This bottom stream can be guided to an oligomerization (not shown). The vapour stream BS1 can also be withdrawn at the top of the distillation column in the form of multiple substreams BS1*n* where n is an integer and is equal to the number of substreams. The same also applies to the bottom stream. The temperature at the bottom of the first distillation column DK1 is preferably in the range from 40 to 110° C., preferably 50 to 100° C.

In principle, the raffinate 2 stream can be directed into the first distillation column DK1 via one or more feed points. If significant variations in the feed concentration are to be expected, it may be advisable to provide multiple different feed points. The optimal position thereof may be found, for example, by simulation via minimization of the energy demand. If multiple feed streams of different composition are to be processed, the optimal feed point can be determined analogously for each feed. It is also possible in principle that the raffinate 2 stream is divided into multiple substreams beforehand even in the case of identical or constant composition. In this case, the raffinate 2 stream is directed into distillation column DK1 in the form of two or more separate streams. It is advantageous here when the feed points of the individual streams are essentially at the same height on distillation column DK1.

The pressure and temperature of the vapour stream BS1 are specified hereinafter. This relates in particular to the pressure and temperature of the at least one vapour stream BS1 when it is withdrawn from distillation column DK1. The pressure of the vapour stream BS1 is especially in the range from 6 to 15 bar absolute, preferably in the range from 7.5 to 13 bar absolute. The temperature of the vapour stream BS1 is especially in the range from 45° C. to 120° C., preferably in the range from 48° C. to 100° C., further preferably in the range from 50° C. to 90° C., further preferably in the range from 55° C. to 80° C., more preferably in the range from 60° C. to 80° C.

The distillation column DK1 used for the separation of the raffinate 2 stream may be any distillation column known to the person skilled in the art. Distillation column DK1 preferably contains internals. Suitable internals are for example trays, unstructured packings (random packings) or structured packings. Trays used are typically bubble-cap trays, sieve trays, valve trays having fixed or movable valves, tunnel-cap trays or slotted trays. Unstructured packings are generally beds of random packings. Random packings used are typically Raschig rings, Pall rings, Berl saddles, Super-Rings/Super-Rings Plus or Intalox® saddles. Structured packings are sold for example under the Mellapak® trade name by Sulzer. In addition to the internals mentioned, further suitable internals are known to those skilled in the art and may likewise be used.

Preferred internals have a low specific pressure drop per theoretical plate. Structured packings and random packing elements have, for example, a significantly lower pressure drop per theoretical plate than trays. This has the advantage that the pressure drop in distillation column DK1 remains as low as possible and hence the mechanical output of the compressor and the temperature of the raffinate 2 stream to be evaporated remains low.

In a particularly preferred embodiment of the present invention, distillation column DK1 comprises a multitude of trays, preferably between 150 and 300 trays, further preferably between 170 and 220 trays.

What is meant in the context of the present invention by the withdrawal of the at least one vapour stream BS1 comprising at least 1-butene and isobutane at the top of distillation column DK1 is in particular that the at least one vapour stream BS1 is withdrawn as top stream or as side draw above the internals in distillation column DK1.

What is meant in the context of the present invention by the withdrawal of the at least one bottom stream comprising at least 1-butene and 2-butene at the bottom of distillation column DK1 is in particular that the at least one bottom stream is withdrawn directly at the bottom or at the lower tray of distillation column DK1.

Distillation column DK1 is preferably operated with reflux. What is meant by "reflux" is that the vapour stream BS1 withdrawn at the top end of distillation column DK1 is at least partly fed back to distillation column DK1. In the cases where such a reflux is established, the reflux ratio is preferably 2 to 30, more preferably 5 to 20, especially preferably 8 to 15.

A reflux can be established by mounting a condenser at the top of distillation column DK1. Vapour stream BS1 is partly condensed in the condenser and fed back to distillation column DK1. The vapour stream can also be applied as reflux to the distillation column only after compression and expansion. In general and in the context of the present invention, a reflux ratio means the ratio of the proportion of the mass flow rate withdrawn from the column (kg/h) that is returned back into the column in liquid form (reflux) to the proportion of that mass flow rate (kg/h) which is discharged from the respective column in liquid form or gaseous form.

After the withdrawal of vapour stream BS1, vapour stream BS1 is compressed, giving rise to a compressed stream VB1 relative to vapour stream BS1. It may be advantageous to heat stream BS1 prior to compression in order that no biphasic mixture is formed on compression. The heating can be conducted by means of internal (see WT1 in FIGS. 6 and 7 of the present application) or external heat sources. The pressure of VB1 after the compression is higher than the pressure of BS1. The exact value for the pressure of VB1 can be set by the person skilled in the art depending on the requirements in the subsequent energy transfer, provided that the condition that pressure VB1>pressure BS1 is met. The quotient of pressure VB1/pressure BS1 (pressures each in bar abs.) is preferably in the range from 1.1 to 10, more preferably 1.2 to 8, more preferably 1.25 to 7, most preferably 1.3 to 6.

The temperature of substream VB1 is preferably higher than the temperature of vapour stream BS1, and the quotient of temperature VB1/temperature BS1 (temperature in each case in K) is preferably in the range from 1.03 to 10, more preferably 1.04 to 9, more preferably 1.05 to 8, more preferably 1.06 to 7, more preferably 1.07 to 6, most preferably 1.08 to 5.

The at least one portion of vapour stream BS1 can be compressed in step (b) in any desired manner known to the person skilled in the art. For example, the compression can be performed mechanically and in a single-stage or multistage compression. What is meant by "single-stage" in this connection is that compression takes place from one pressure level to another. What is meant by "multistage" is that compression is effected first to a pressure level X and then from X to the pressure level Y. In a multistage compression, it is possible to use two or more compressors of the same type or compressors of different types. A multistage compression can preferably be effected with one compressor machine or with multiple compressor machines. The use of single-stage compression or multistage compression depends on the compression ratio and hence on the pressure to which the vapour stream BS1 is to be compressed.

A suitable compressor in the process according to the invention, especially for compression of the vapour stream BS1 to VB1, is any compressor known to the person skilled in the art, preferably mechanical compressor, with which gas streams can be compressed. Suitable compressors are, for example, single-stage or multistage geared turbocompressors, piston compressors, screw compressors, centrifugal compressors or axial compressors.

In step (c) of the process according to the invention, energy is transferred from the compressed stream VB1 to the stream in reboiler SV1. Step (c) lowers the energy of VB1, such that VB1 can be partly condensed. According to the invention, the phrase "transfer of energy" especially means "heating", i.e. transfer of energy in the form of heat.

The transfer of energy from VB1 to the stream in the reboiler SV1, preferably the heating of the stream in the reboiler SV1 by VB1, is preferably direct. What is meant by direct transfer is that VB1 and the stream in SV1 do not come into direct contact, but energy, especially heat, is transferred from VB1 to the stream in SV1 without the presence of any additional heat transfer medium. Reboilers SV1 used may be the heat transferrers or heat exchangers that are familiar to the person skilled in the art, especially evaporators.

Before stream VB1 is guided to the second distillation column by step (d) to the second distillation column, stream VB1, in a preferred embodiment, is guided to a flash vessel and expanded therein to obtain a liquid phase FP1. The flash vessel may additionally comprise a condenser in order to condense a portion of the gaseous phase obtained.

At least a portion FP1*a* of the liquid phase FP1 is then directed in step (d) to distillation column DK2. For this purpose, in a particularly preferred embodiment, a pump is used. It is possible here to use pumps known to the person skilled in the art. Suitable pumps are, for example, standard chemical pumps.

It is further preferable that a portion FP1*b* of the liquid phase FP1 other than FP1*a* is returned as reflux to the first distillation column DK1. It is particularly preferable that this transfers energy from stream FP1*b* to the raffinate 2 stream before the raffinate 2 stream is introduced into the first distillation column DK1. This preheats the raffinate 2 stream. This is energetically advantageous because less energy has to be introduced for the separation task via the reboilers. The transfer of energy from FP1*b* to the raffinate 2 stream, preferably the heating of the raffinate 2 stream by FP1*b*, is preferably direct, i.e. without use of a (further) heat transfer medium. For this purpose, it is possible to use heat transferrers or heat exchangers that are familiar to the person skilled in the art.

Streams VB1 or FP1*a* are thus guided to the second distillation column DK2. If the amounts of isobutene in stream VB1 or in stream FP1*a* are too high to meet the specification for the 1-butene product from DK2, it is possible, as mentioned, for an additional MTBE or ETBE synthesis to be disposed between distillation columns DK1 and DK2. For this purpose, stream VB1 or stream FP1*a* is guided to an MTBE or ETBE synthesis, and the isobutene present is at least partly converted to MTBE or ETBE.

MTBE or ETBE synthesis is known in principle to those skilled in the art. For the preparation of MTBE or ETBE from isobutene-containing streams, it is possible in particular to use acidic ion exchange resins (sulfo groups) as heterogeneous catalysts. The MTBE or ETBE synthesis may take place in one or more series-connected reactors. The catalyst is preferably used in the form of a fixed bed catalyst. Since the formation of MTBE or ETBE is an equilibrium reaction, it may be appropriate to use at least one reactive distillation column in which the reaction and removal of the MTBE or ETBE are simultaneous. In the reactive distillation, the pressure should be in the range from 3 to 15 bar and the temperature in the reaction zone from 55 to 75° C.

After the synthesis, MTBE or ETBE is separated from stream VB1 or FP1*a*, preferably by distillation. This method is also known to the person skilled in the art. Only then is VB1 or FP1*a* guided to distillation column DK2.

In the second distillation column DK2, the streams that both respectively comprise at least isobutane and 1-butene are separated in step (d) into at least one vapour stream BS2 which comprises at least isobutane and is withdrawn at the top of DK2, and at least one product stream which comprises at least 1-butene and is withdrawn at the bottom of DK2.

The distillation column DK2 used for the separation of the raffinate 2 stream may be any distillation column known to the person skilled in the art. Distillation column DK2 preferably contains internals. Suitable internals are for example trays, unstructured packings (random packings) or structured packings. Trays used are typically bubble-cap trays, sieve trays, valve trays having fixed or movable valves, tunnel-cap trays or slotted trays. Unstructured packings are generally beds of random packings. Random packings used are typically Raschig rings, Pall rings, Berl saddles, Super-Rings/Super-Rings Plus or Intalox® saddles. Structured packings are sold for example under the Mellapak® trade name by Sulzer. In addition to the internals mentioned, further suitable internals are known to those skilled in the art and may likewise be used.

Preferred internals have a low specific pressure drop per theoretical plate. Structured packings and random packing elements have, for example, a significantly lower pressure drop per theoretical plate than trays. This has the advantage that the pressure drop in distillation column DK2 remains as low as possible and hence the mechanical output of the compressor and the temperature of the stream to be evaporated remains low.

In a particularly preferred embodiment of the present invention, the second distillation column DK2 comprises a multitude of trays, preferably between 150 and 300 trays, further preferably between 170 and 220 trays.

What is meant in the context of the present invention by the withdrawal of the at least one vapour stream BS2 comprising at least isobutane at the top of distillation column DK2 is in particular that the at least one vapour stream BS2 is withdrawn as top stream or as side draw above the internals in distillation column DK2.

What is meant in the context of the present invention by the withdrawal of the at least one product stream comprising at least 1-butene at the bottom of distillation column DK2 is in particular that the at least one product stream is withdrawn directly at the bottom or at the lower tray of distillation column DK2. The product stream preferably contains at least 99% by weight of 1-butene, further preferably at least 99.5% by weight of 1-butene, more preferably at least 99.6% by weight of 1-butene. The 1-butene is the target product of the present process, and therefore the product stream is discharged from the process. The 1-butene may be used, for example, as a comonomer in the production of polyethylene.

It should be noted here that the separation sharpness in the first distillation column DK1 ultimately determines the purity of the 1-butene in the product stream which is withdrawn from the second distillation column DK2. This is because n-butane and the 2-butenes are likewise obtained as high boilers in DK2, and therefore with the 1-butene. This would contaminate the 1-butene. It should thus be ensured that the separation of the raffinate 2 stream in DK1 is run as far as possible such that barely any n-butane gets to DK2. It is therefore preferable that the stream guided to DK2 (1*a*, VB1 or FP1*a*) contains below 1500 ppm, preferably below 1200 ppm, more preferably below 900 ppm, of n-butane, based on the total amount of the stream.

The temperature at the bottom of the second distillation column DK2 during the process according to the invention is preferably in the range from 30 to 100° C., preferably 45 to 80° C. Further preferably, the pressure at the top of the second distillation column DK2 is in the range from 3 to 12 bar absolute, preferably 5 to 10 bar absolute.

Distillation column DK2 can also be operated with reflux. What is meant by "reflux" is that the vapour stream BS2 withdrawn at the top end of distillation column DK2 is at least partly fed back to distillation column DK2. In the cases where such a reflux is established, the reflux ratio is preferably 10 to 100, especially preferably 30 to 50.

The pressure ranges for the top pressure, i.e. the pressure at the top of distillation columns DK1 and DK2, was defined in the preceding paragraphs. In principle, it would accordingly be possible for the two columns to be operated in a dual-pressure connection, i.e. at a different pressure. It is then possible to transfer energy from the high-pressure column to the low-pressure column, in addition to the vapour compression described here. However, it is preferable in accordance with the invention that distillation columns DK1 and DK2 are operated at the same top pressure or a similar top pressure, where the top pressures in the case of similar top pressures differ by not more than 20%, preferably not more than 15%. Another advantageous factor, aside from a lower apparatus complexity, is a lower energy input. Finally, relative volatility will fall with rising pressure, and the required amount of energy for the separation task to be accomplished will become much greater in at least the high-pressure column.

Subsequently, in step (e), the vapour stream BS2 is at least partly compressed, giving rise to a compressed stream VB2 relative to the vapour stream BS2. The pressure of VB2 after the compression is higher than the pressure of BS2. The exact value for the pressure of VB2 can be set by the person skilled in the art depending on the requirements in the subsequent energy transfer, provided that the condition that pressure VB2>pressure BS2 is met. The quotient of pressure VB2/pressure BS2 (pressures each in bar abs.) is preferably in the range from 1.1 to 10, more preferably 1.2 to 8, more preferably 1.25 to 7, most preferably 1.3 to 6. It may be advantageous to heat stream BS2 prior to compression in order that no biphasic mixture is formed on compression. The heating can be conducted by means of internal (see WT-2 in FIGS. 6 and 7 of the present application) or external heat sources.

The temperature of substream VB2 is especially higher than the temperature of vapour stream BS2, and the quotient of temperature VB2/temperature BS2 (temperature in each case in K) is preferably in the range from 1.03 to 10, more preferably 1.04 to 9, more preferably 1.05 to 8, more preferably 1.06 to 7, more preferably 1.07 to 6, most preferably 1.08 to 5.

The at least one portion of vapour stream BS2 can be compressed in step (e) in any desired manner known to the person skilled in the art. For example, the compression can be performed mechanically and in a single-stage or multistage compression. In a multistage compression, it is possible to use two or more compressors of the same type or compressors of different types. A multistage compression can be effected with one or more compressor machines. The use of single-stage compression or multi-stage compression depends on the compression ratio and thus on the pressure to which vapour stream BS2 is to be compressed.

A suitable compressor in the process according to the invention, especially for compression of the vapour stream BS2 to VB2, is any compressor known to the person skilled in the art, preferably mechanical compressor, with which gas streams can be compressed. Suitable compressors are, for example, single-stage or multistage turbines, piston compressors, screw compressors, centrifugal compressors or axial compressors.

In step (f) of the process according to the invention, energy is transferred from the compressed stream VB2 to the stream in reboiler SV2. Step (f) lowers the energy of VB2, such that VB2 can be at least partly condensed. According to the invention, the phrase "transfer of energy" especially means "heating", i.e. transfer of energy in the form of heat.

The transfer of energy from VB2 to the stream in the reboiler SV2, preferably the heating of the stream in the reboiler SV2 by VB2, is preferably direct. What is meant by direct transfer is that VB2 and the stream in SV2 do not come into contact, but energy, especially heat, is transferred from VB2 to the stream in SV2 without the presence of any additional heat transfer medium. Reboilers SV2 used may be the heat transferrers or heat exchangers that are familiar to the person skilled in the art, especially evaporators.

Once stream VB2 has passed through reboiler SV2 and transferred energy to the stream present therein, VB2 can be discharged from the process as isobutane stream IB1. But before VB2 is removed from the process as IB1, stream VB2, in a preferred embodiment of the present invention, is guided to a flash vessel and expanded therein to obtain a liquid phase FP2. The flash vessel may additionally comprise a condenser in order to condense a portion of the gaseous phase obtained.

At least a portion FP2*a* of the liquid phase FP2 can then be discharged from the process as isobutane stream IB1. For this purpose, in a particularly preferred embodiment, a pump is used. Under some circumstances and given a sufficient pressure ratio, it would also be possible that no pump is used. If a pump is used, it is possible to use pumps known to the person skilled in the art. Suitable pumps are, for example, standard chemical pumps. It is further preferable that a portion FP2*b* of the liquid phase FP1 other than FP2*a* is returned as reflux to the first distillation column DK2.

In the basic configuration of the present invention, the two streams BS1 and BS2 are each compressed with a single compressor. In a preferred embodiment of the present invention, the two streams BS1 and BS2 are compressed in a single compressor machine, preferably in multiple stages. The number of stages needed depends on the target compression ratio for the respective vapour streams BS1 and BS2.

The thermal integration by means of the vapour compression described here would also be combinable with other measures for thermal integration. It would also be possible here to provide one or more heat pump(s).

The present invention is hereinbelow elucidated with reference to figures. The figures are for illustration but are not to be understood as limiting.

FIG. 1 shows an embodiment according to the prior art without the thermal integration according to the invention. The raffinate 2 stream (1) is directed to the first distillation column DK1, where it is separated into a vapour stream BS1 which comprises at least 1-butene and isobutane and is withdrawn at the top of DK1, and into a bottom stream (2) which comprises at least 1-butene and 2-butene and is withdrawn at the bottom of DK1. This stream (2) can be conducted to an oligomerization (not shown). The energy input into distillation column DK1 is effected by transferring energy to the stream in reboiler SV1. Vapour stream BS1 is at least partly condensed by means of a cooling apparatus (K1), for example an air cooler or a heat transferrer operated with cooling water, and run to a reservoir vessel where the liquid phase FP1 and FP1*w* may arise. This organic liquid phase (FP1) is separated into the two streams FP1*a*, which is conducted to the second distillation column DK2, and FP1*b*, which is directed as reflux to the first distillation column. In addition, it is possible to separate off a heavy aqueous phase (5). In distillation column DK2, separation is effected into a vapour stream BS2 which comprises at least isobutane and is withdrawn at the top of DK2, and a product stream (3) which comprises at least 1-butene and is withdrawn at the bottom of DK2. The energy input into distillation column DK2 is effected by transferring energy to the stream in reboiler SV2. The transfer is effected with heating steam.

Figure 2:
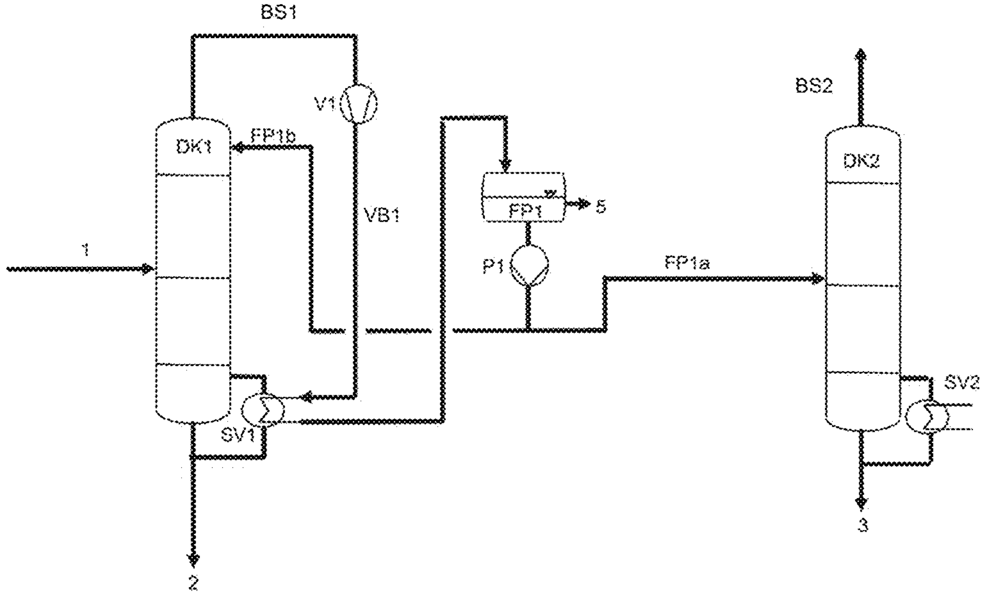
FIG. 2 shows a non-inventive configuration in which heat recovery takes place only in distillation column DK1.

FIG. 2 likewise shows a non-inventive embodiment in which heat recovery takes place only in distillation column DK1. By contrast with the embodiment shown in FIG. 1, in the present context, vapour stream BS1 is brought to a higher pressure with a compressor V1 and then directed to reboiler SV1 as stream VB1. Energy is transferred in reboiler SV1 to the stream present therein, which is heated coming from the bottom and then returned again, in order to introduce the energy needed for the separation. VB1 is then guided to the flash vessel, where liquid phase FP1 is obtained, which is run as reflux FP1*b* back to the uppermost plate of the column, and as FP1*a* as feed to DK2. In addition, it is possible to separate off a heavy aqueous phase (5).

Figure 3:
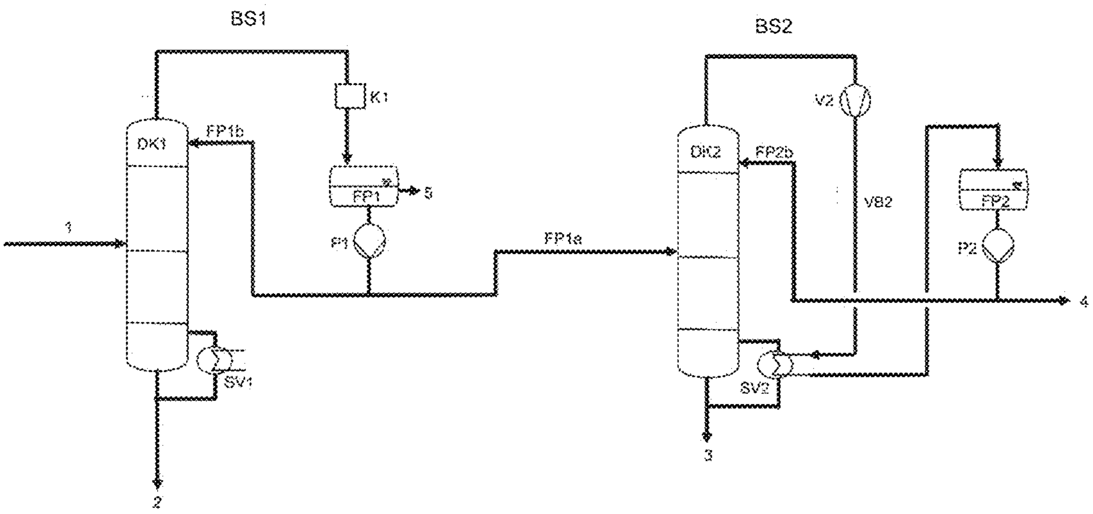
FIG. 3 shows a non-inventive configuration in which thermal integration takes place only in distillation column DK2.

FIG. 3 likewise shows a non-inventive embodiment in which thermal integration takes place only in distillation column DK2. By contrast with the embodiment shown in FIG. 1, in the present context, vapour stream BS2 is brought to a higher pressure with a compressor V2 and then directed to reboiler SV2 as stream VB2. Energy is transferred in reboiler SV2 to the stream present therein, which is heated coming from the bottom and then returned again, in order to introduce the energy needed for the separation. Stream VB2 is run to a flash vessel, where the expansion results in a liquid phase FP2. This liquid phase (FP2) is separated into the two streams FP2*b*, which is returned as reflux to the second distillation column DK2, and an isobutane stream (4) which is discharged from the process. In addition, it is possible to separate off a heavy aqueous phase (5).

Figure 4:
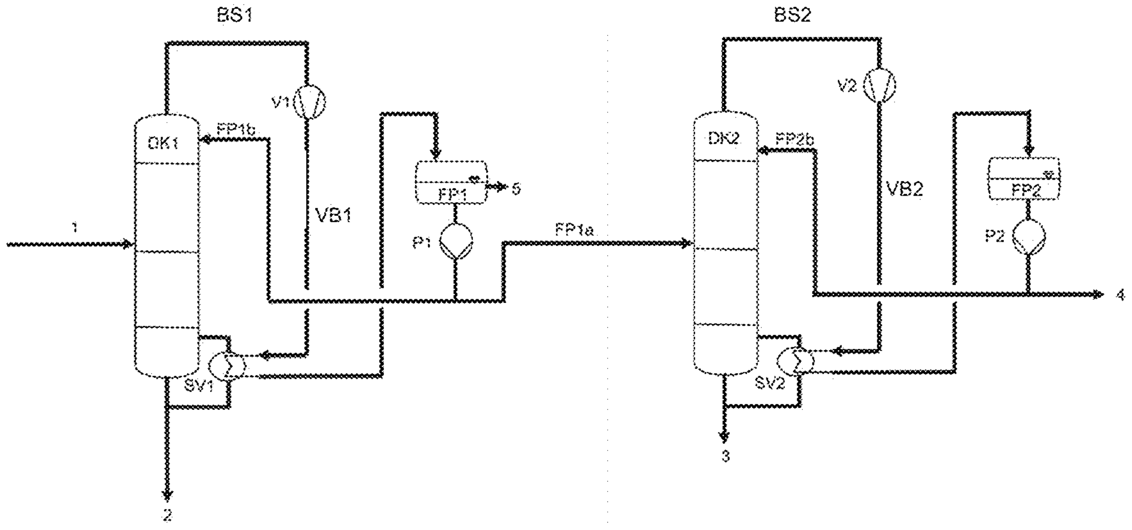
FIG. 4 shows the basic configuration of the present invention.

FIG. 4 shows the basic configuration of the present invention. The raffinate 2 stream (1) is directed to the first distillation column DK1, where it is separated into a vapour stream BS1 which comprises at least 1-butene and isobutane and is withdrawn at the top of DK1, and into a bottom stream (2) which comprises at least 1-butene and 2-butene and is withdrawn at the bottom of DK1. This stream (2) can be conducted to an oligomerization (not shown). Vapour stream BS1 is brought to a higher pressure with compressor V1 and then guided as stream VB1 to reboiler SV1, where it transfers energy to the stream present therein, which is heated coming from the bottom and then returned again. Stream VB1 is then run to a flash vessel, where the expansion results in a liquid phase FP1. This liquid phase (FP1) is separated into the two streams FP1*a*, which is conducted to the second distillation column DK2, and FP1*b*, which is returned as reflux to the first distillation column DK1. In distillation column DK2, separation is effected into a vapour stream BS2 which comprises at least isobutane and is withdrawn at the top of DK2, and separated into a product stream (3) which comprises at least 1-butene and is withdrawn at the bottom of DK2. Vapour stream BS2 is brought to a higher pressure with compressor V2 and then directed as stream VB2 for the transfer of energy to the stream in reboiler SV2. Stream VB2 is then run to a flash vessel, where the expansion results in a liquid phase FP2. This liquid phase (FP2) is separated into the two streams FP2*b*, which is returned as reflux to the second distillation column DK2, and an isobutane stream (4) which is discharged from the process. If the feed to DK1 contains traces of water, it may be separated off from the flash vessels of DK1 and DK2 as heavy aqueous phase (5). It is thus possible to minimize the water content of product streams 2 and 3.

Figure 5:
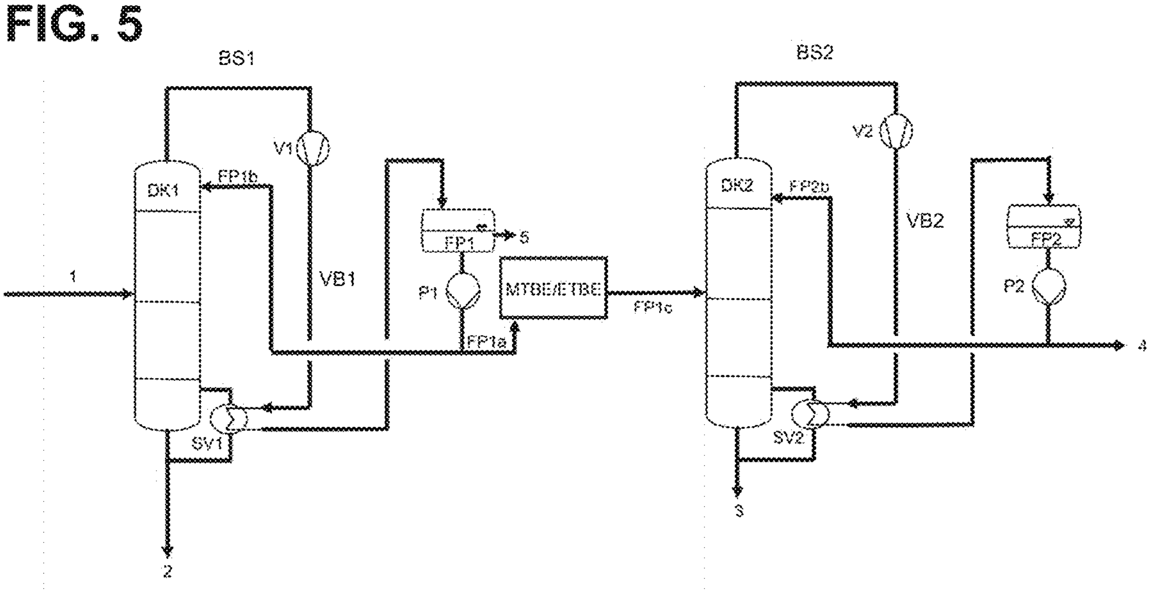
FIG. 5 shows a configuration in which stream FP1*a* is not conducted directly to distillation column DK2.

FIG. 5 shows a further embodiment according to the present invention. The difference from FIG. 4 is that stream FP1*a* is not conducted directly to distillation column DK2. Instead, the stream still contains certain amounts of isobutene that would be obtained in, and would contaminate, the product stream (3) in the separation in DK2. Therefore, stream FP1*a* is run to an MTBE or ETBE unit, where isobutene is first reacted with methanol to give MTBE or ethanol to give ETBE, and then a separation from MTBE takes place, for example with involvement of a reactive distillation column. Stream FP1*c* obtained from the MTBE unit contains little to no MTBE and is, as described for FIG. 4, separated in distillation column DK2.

Figure 6:
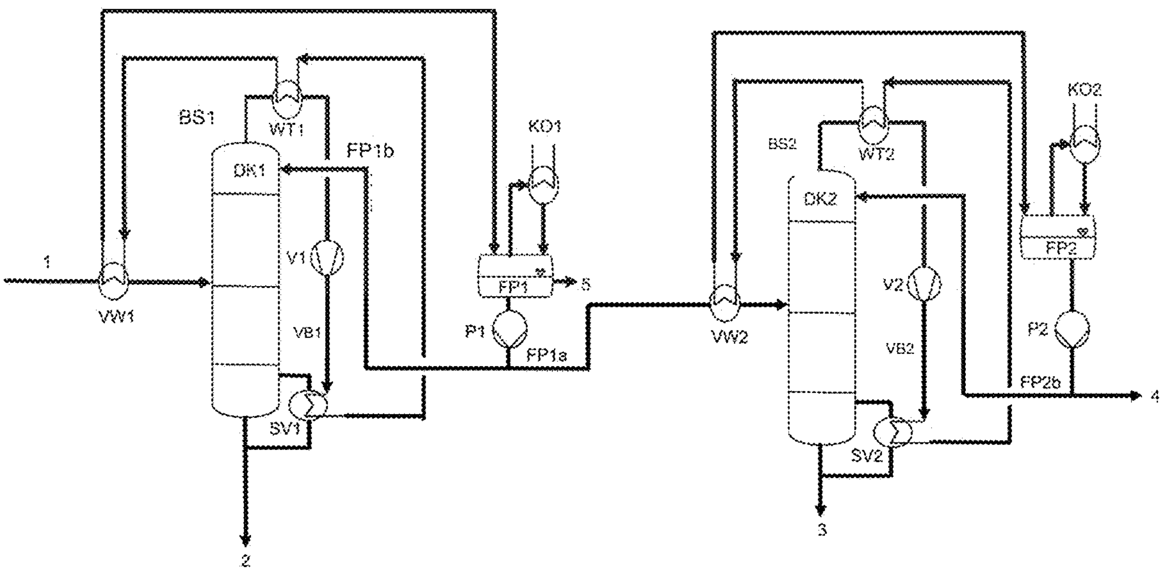
FIG. 6 shows a configuration in which there are two additional heat exchangers (WT1, WT2) via which energy is transferred from streams VB1 (in WT1) and VB2 (in WT2) for superheating to streams BS1 (in WT1) and BS2 (in WT2).

FIG. 6 shows a further embodiment according to the present invention. The difference from FIG. 4 is firstly that there are two additional heat exchangers (WT1, WT2) via which energy is transferred from streams VB1 (in WT1) and VB2 (in WT2) for superheating to streams BS1 (in WT1) and BS2 (in WT2). This can prevent the vapour streams from entering the biphasic region on compression, and ensure that no droplets that can damage the compressor are formed. Moreover, streams VB1 and VB2 in heat transferrers VW1 and VW2 can additionally release energy to the feed streams of DK1 and DK2, which reduces the energy demand of the reboilers SV1 and SV2 and hence the power to drive compressors V1 and V2. A further difference from FIG. 4 is that a condenser (KO1, KO2) for closed-loop control of the pressure is installed in each of the two flash vessels. In addition, the condensers can also be used for the startup process.

Figure 7:
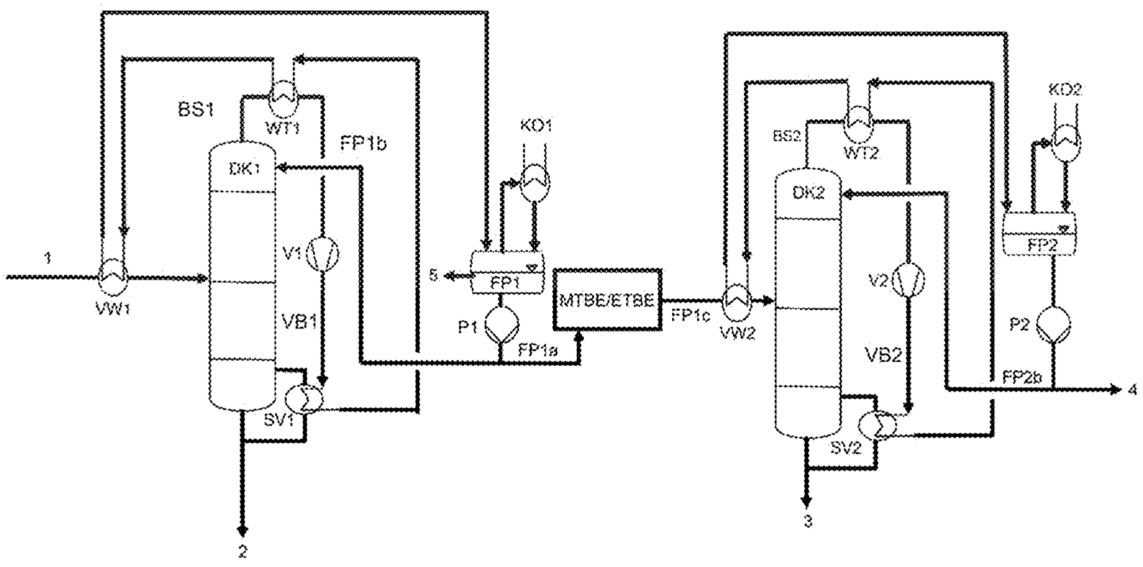
FIG. 7 shows a configuration in which stream FP1*a* is not conducted directly to distillation column DK2.

FIG. 7 shows a further embodiment of the present invention. The difference from FIG. 6 is that stream FP1*a* is not conducted directly to distillation column DK2. Instead, the stream still contains certain amounts of isobutene that would be obtained in, and would contaminate, the product stream (3) in the separation in DK2. Therefore, stream FP1*a* is run to an MTBE or ETBE unit, where isobutene is first reacted with methanol to give MTBE or ethanol to give ETBE, and then a separation from MTBE takes place, for example with involvement of a reactive distillation column. Stream FP1*c* obtained from the MTBE unit contains little to no MTBE is, as described above, separated in distillation column DK2.

Figure 8:
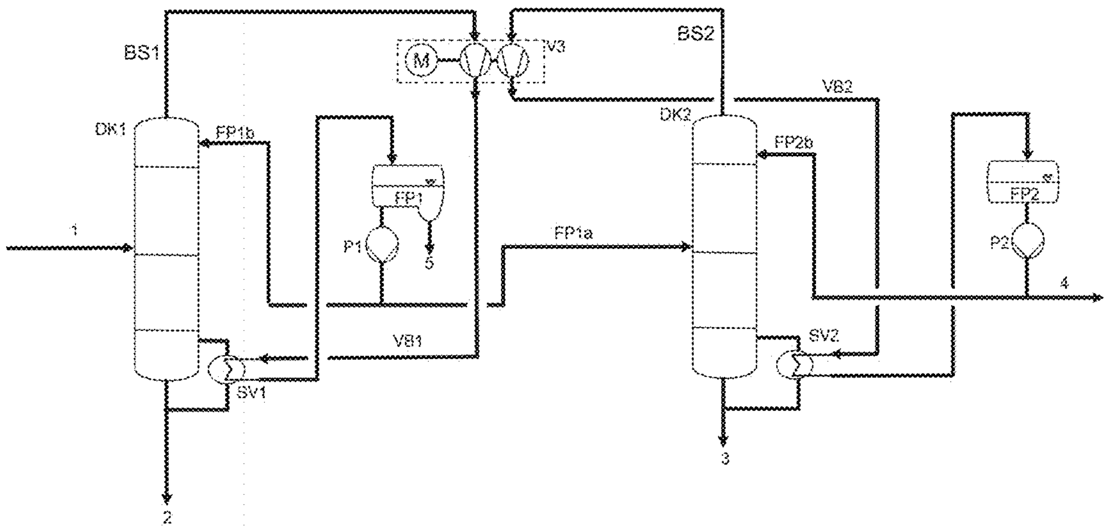
FIG. 8 shows a configuration in which a compressor (V3) with multiple compressor machines is used.

FIG. 8 shows a further embodiment of the present invention. The difference from FIG. 4 is that a compressor (V3) with multiple compressor machines is used here. For instance, it is possible that the compression of BS1 and BS2 takes place independently in a compressor. Moreover, the heavy aqueous phase (5) is separated off here by means of an udder, indicated by means of the bulge.

Figure 9:
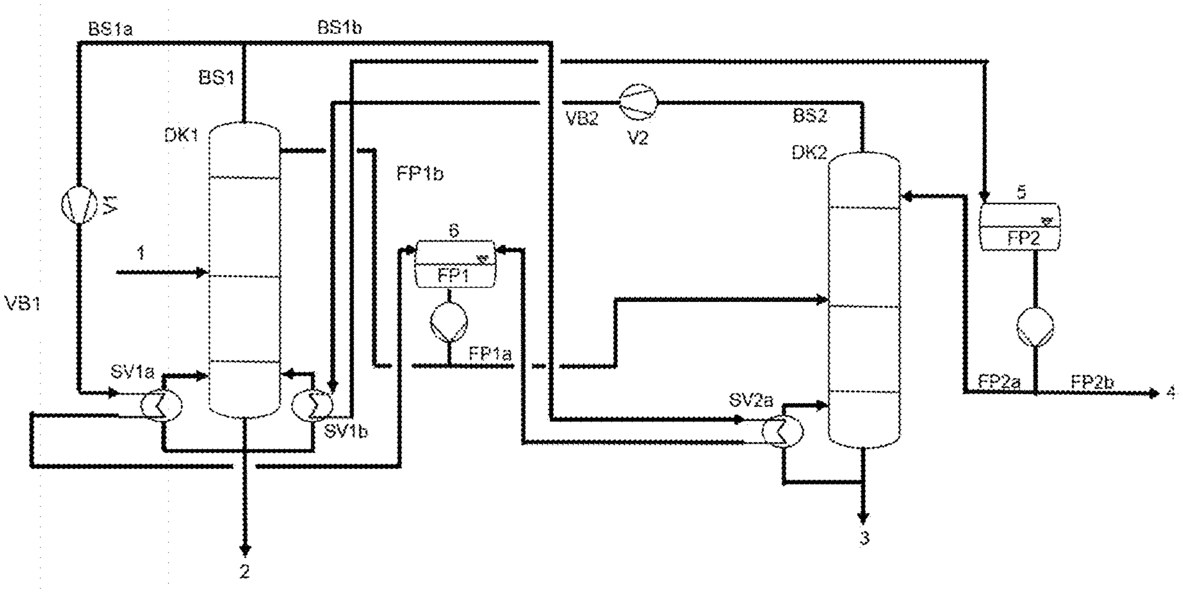
FIG. 9 shows a configuration in which the two distillation columns have different pressures and the vapour compression is linked differently.

FIG. 9 shows an alternative configuration in which the two distillation columns have different pressures and the vapour compression is linked differently. The raffinate 2 stream (1) is guided to the first distillation column DK1, where it is separated into a vapour stream BS1 which comprises at least 1-butene and isobutane and is withdrawn at the top of DK1, and a bottom stream (2) which comprises at least 1-butene and 2-butene and is withdrawn at the bottom of DK1. Vapour stream BS1 is separated into the two vapour streams BS1*a* und BS1*b*. BS1*a* is brought to a higher pressure with compressor V1 and then directed as stream VB1, for energy transfer, to the stream in the reboiler SV1*a*. The second portion BS1*b* of the vapour stream is conducted without additional compression to reboiler SV2*a*, where it transfers energy to the stream present therein, which is heated coming from the bottom and is then returned again. The two streams VB1 and BS1*b*, after the transfer of energy, are run to a flash vessel, where the expansion gives rise to a liquid phase FP1. This liquid phase is separated into the two streams FP1*a*, which is conducted to the second distillation column DK2, and FP1*b*, which is directed as return stream to the first distillation column. In distillation column 2, the streams are separated into a vapour stream BS2 which comprises at least isobutane and is withdrawn at the top of DK2, and a product stream (3) which comprises at least 1-butene and is withdrawn at the bottom of DK2. Vapour stream BS2 is brought to a higher pressure with compressor V2 and then directed as stream VB2, for energy transfer, to the stream in reboiler SV1*b*. VB2 then ends up in a flash vessel and at least partly condenses as liquid phase FP2, from which a portion FP2*a* of isobutane stream (4) leaves the process and another portion FP2*b* is recycled to the second distillation column as return stream.

EXAMPLES

For all the examples that follow, a raffinate 2 stream of 55 t/h was used. The raffinate 2 stream has the following composition: 1-butene 45.1%/n-butane 22.4%/trans-2-butene 15.9%/cis-2-butene 8.9%/isobutane 7.4%/isobutene 300 ppm and water 590 ppm.

The amount of energy needed for operation of the plants detailed in the examples for separation of 1-butene from raffinate 2 was calculated by a simulation using Aspen V10. The physical data were validated by operational data and operational trials.

Example 1 (not According to the Invention)

In the embodiment shown in FIG. 1, the raffinate 2 in the above-specified composition is run to distillation column DK1. The column is operated at a top pressure of 6 bar abs. The top temperature is 43° C. 140 theoretical trays are included in the simulation. A 1-butene-depleted stream (raffinate 3) is drawn off via the bottom of the column. The bottom temperature is 62° C. A pressure drop of 1000 mbar in DK1 is included in the simulation. A distillate stream in an amount of 15.2 t/h is drawn off via the top, containing about 77 wt % of 1-butene and about 22 wt % of isobutane. The distillation in DK1 requires a heating output of 15 MW, which is introduced into the column by means of heating steam via reboiler SV1.

The second distillation column DK2 is operated in a similar manner. For separation of the 1-butene from the isobutane from the distillate stream from DK1, a heating output of 10.2 MW is introduced in the second column DK2 by heating steam in reboiler SV2. In the bottom of DK2, 11.6 t/h of product stream is drawn off with a purity of 99.6 wt % of 1-butene. 3.6 t/h is drawn off at the top of DK2. The distillate stream consists to an extent of 95% of isobutane. The column is likewise operated at a top pressure of 6 bar abs. and a top temperature of 40° C. The pressure drop for 140 vertical trays is 1000 mbar. A bottom temperature of 56.6° C. is established.

Overall, in the interconnection shown in FIG. 1, it is necessary to use 25.2 MW of externally provided heating steam.

Example 2 (not According to the Invention)

A further trial was conducted with the interconnection shown in FIG. 2. By contrast with FIG. 1 and Example 1, there is a vapour compression in distillation column DK1. For this purpose, the vapour stream from DK1, BS1, is compressed by compressor V1 to 11 bar abs. The result is the compressed vapour stream VB1, which can be condensed in reboiler SV1. At 11 bar abs., the compressed vapour stream condenses at 73° C. The compression operation requires an electrical power of 1.6 MW. 15 MW can be transferred via SV1.

Overall, in the interconnection shown in FIG. 2, it is necessary to use 10.2 MW of externally provided heating steam and 1.6 MW of electrical power.

Example 3 (not According to the Invention)

A further trial was conducted with the interconnection shown in FIG. 3. By contrast with FIG. 1 and Example 1, there is a vapour compression in distillation column DK2. For this purpose, an electrical power of 1.0 MW is needed to compress the vapour BS2 to a higher pressure level of 11.7 bar abs. and hence to render the heat of condensation utilizable in SV2. It is possible to transfer 10.2 MW.

Overall, in the interconnection shown in FIG. 3, it is necessary to use 15 MW of externally provided heating steam and 1.0 MW of electrical power.

Example 4 (According to the Invention)

A further trial was conducted with the interconnection shown in FIG. 4. The thermal integration according to the invention is provided here for both distillation columns DK1 and DK2. For this purpose, it is possible to install either a single compressor having at least two stages or to use two individual compressors. Both vapour streams are compressed to the required pressure level (see Examples 2 and 3) in order to create a driving temperature difference of about 10 K and hence to recirculate the heat of condensation into the process. It is thus possible to fully electrify both columns DK1 and DK2 in the interconnection shown.

In the embodiment shown in FIG. 4, it is not necessary to use any externally provided heating steam. Only 2.6 MW of electrical power is needed for operation of the compressors.

Example 5 (According to the Invention)

A further trial was conducted with the interconnection shown in FIG. 6, in which the differences from FIG. 4 included the additional vapour streams BS1 and BS2 and preheating of the feed streams. Excess heat which arises via the introduction of electrical power need not be withdrawn via an additional cooling operation, but is used for preheating of the vapour streams in heat exchangers WT1 and WT2, and the feed streams in preheaters VW1 and VW2. Accordingly, the electrical power of 2.6 MW required in the compressors can be reduced in Example 4 to a total of 2.3 MW. There is likewise no need here to use externally provided heating steam.

Example 6 (According to the Invention)

A further trial was conducted with the interconnection shown in FIG. 7, in which the difference from FIG. 6 was the presence of an MTBE unit. In the interconnections shown here, the isobutene goes overhead in DK1 and remains in the bottom of DK2. It thus follows the 1-butene, and is barely separable from the 1-butene in this interconnection. Accordingly, an increase in concentration takes place. If a second MTBE stage is then included between DK1 and DK2, it is possible to reduce the isobutene concentration in the 1-butene. It is therefore no longer necessary to run the separation of n-butane in column DK1 as sharply. Moreover, it is possible to leave more isobutane in the bottom. Overall, it is thus possible to save a further 200 KW of electrical power.

Example 7 (not According to the Invention)

In this embodiment, direct heat integration is conducted between columns DK1 und DK2 (as disclosed in DE 10 2005 062 700 A1) and is supplemented in accordance with the invention with a multistage vapour compression (see FIG. 9). In this case, column DK1 is operated at a top pressure of 11 bar and column DK2 at a top pressure of 7 bar. It is thus possible to use a portion of vapour stream BS1 to transfer heat via reboiler SV2*a* in DK2. A heat of condensation of 4.0 MW from DK1 is rendered utilizable via a one-stage vapour compression by means of compressor V1 and introduced via a second reboiler SV1*a* in DK1. For this purpose, 382 KW of electrical power has to be applied in compressor V1. In addition, the vapour from DK2 is compressed in order to render the heat of condensation of 9.9 MW from DK2 utilizable for DK1. The heat of condensation upgraded by means of compressor V2 is transferred via a further reboiler SV1*b*. For this purpose, an electrical power of 2.6 MW is required. It is possible to transfer a total of 11.5 MW via SV1*b* by use of 2.98 MW of electrical energy.

The results of Examples 1 to 7 are summarized below in Table 1.

TABLE 1

Summary of the examples

| | Ex. 1 | Ex. 2 | Ex. 3 | Ex. 4 | Ex. 5 | Ex. 6 | Ex. 7 |
|---|---|---|---|---|---|---|---|
| Externally provided heating output [MW] | 25.2 | 10.2 | 15 | 0 | 0 | 0 | 0 |
| Electrical power for compressor [MW] | 0 | 1.6 | 1.0 | 2.6 | 2.3 | 2.1 | 2.98 |

It is found that the inventive configuration of the process for 1-butene separation has the effect that much less external heating power has to be used than in the known solution. The savings potential is thus considerable. The electrical power additionally required for operation of the compressors is much smaller and can enable $CO_2$-neutral operation when green power is used.

It is also found that an embodiment in which the two distillation columns DK1 and DK2 are operated at different pressure is disadvantageous because it requires the use of a greater amount of electrical energy.

The invention claimed is:

1. A process for separating 1-butene from a raffinate 2 stream containing at least 1-butene, 2-butene, n-butane, isobutene and isobutane in a separation unit comprising a first distillation column DK1 and a second distillation column DK2, wherein the first distillation column DK1 has at least one reboiler SV1 and the second distillation column DK2 has at least one reboiler SV2;

the at least one reboiler SV1 is fed with a stream which is withdrawn at a lower end of the first distillation column DK1 and, after passing through a respective reboiler, is guided back to the first distillation column DK1;

the at least one reboiler SV2 is fed with a stream which is withdrawn at a lower end of the second distillation column DK2 and, after passing through a respective reboiler, is guided back to the second distillation column DK2; the process comprising:

(a) directing the raffinate 2 stream to the first distillation column DK1 and separating the raffinate 2 stream in the first distillation column DK1 into at least one vapour stream BS1 which comprises at least 1-butene and isobutane and is withdrawn at a top of the first distillation column DK1, and at least one bottom stream which comprises at least 1-butene, n-butane and 2-butene and is withdrawn at a bottom of the first distillation column DK1;

(b) compressing at least a portion of the at least one vapour stream BS1, giving rise to a compressed stream VB1 relative to the at least one vapour stream BS1;

(c) transferring energy from the compressed stream VB1 to a stream in the at least one reboiler SV1;

(d) directing the compressed stream VB1 at least partly to the second distillation column DK2 and separating the compressed stream VB1 in the second distillation column DK2 into at least one vapour stream BS2 which comprises at least isobutane and is withdrawn at a top of the second distillation column DK2, and at least one bottom stream which comprises at least 1-butene and is withdrawn at a bottom of the second distillation column DK2;

(e) at least partly compressing the at least one vapour stream BS2, giving rise to a compressed stream VB2 relative to the at least one vapour stream BS2; and (f) transferring energy from the compressed stream VB2 to the stream in the at least one reboiler SV2.

2. The process according to claim 1, further comprising: operating the first distillation column DK1 and the second distillation column DK2 at a same top pressure or a similar top pressure, where top pressures in case of a similar top pressure differ by not more than 20%.

3. The process according to claim 1, further comprising: disposing an MTBE or ETBE synthesis between the first distillation column DK1 and the second distillation column DK2, which is fed with the compressed stream VB1.

4. The process according to claim 1, further comprising: guiding the compressed stream VB1 to a flash vessel, and expanding the compressed stream VB1 in the flash vessel, resulting in a liquid phase FP1 of the compressed stream VB1.

5. The process according to claim 4, further comprising: directing at least a portion FP1*a* of the liquid phase FP1 to the second distillation column DK2.

6. The process according to claim 5, further comprising: returning another portion FP1*b* of the liquid phase FP1 as reflux to the first distillation column DK1.

7. The process according to claim 1, further comprising:

transferring energy from stream FP1*b* to the raffinate 2 stream before the raffinate 2 stream is introduced into the first distillation column DK1.

8. The process according to claim 1, further comprising:

adjusting a temperature in the bottom of the first distillation column DK1 to a range from 40 to 110° C.

9. The process according to claim 1, further comprising:

adjusting a temperature in the bottom of the second distillation column DK2 to a range from 30 to 100° C.

10. The process according to claim 1, wherein the first distillation column DK1 has between 150 and 300 trays.

11. The process according to claim 1, wherein the second distillation column DK2 has between 150 and 300 trays.

12. The process according to claim 1, further comprising:

employing only a single compressor for a compression of the at least one vapour stream BS1 and the at least one vapour stream BS2.

13. The process according to claim 1, further comprising:

expanding the compressed stream VB2 into a flash vessel, where a liquid phase FP2 is obtained.

14. The process according to claim 12, further comprising:

discharging at least a portion FP2*a* of the liquid phase FP2 from the process as product stream.

15. The process according to claim 13, further comprising:

returning another portion FP2*b* of the liquid phase FP2 as reflux to the second distillation column DK2.

16. The process according to claim 1, wherein the first distillation column DK1 and the second distillation column DK2 independently have between 170 and 220 trays.

17. The process according to claim 1, further comprising: adjusting a temperature in the bottom of the first distillation column DK1 to a range from 50 to 100° C. and further comprising adjusting a temperature in the bottom of the second distillation column DK2 to a range from 45 to 80° C.

18. The process according to claim 1, wherein the raffinate 2 stream, comprises less than 2500 ppm of isobutene.

19. The process according to claim 1, wherein the raffinate 2 stream comprises less than 500 ppm of isobutene.

20. The process according to claim 1, wherein the raffinate 2 stream comprises less than 4% by weight of polyunsaturated C4 hydrocarbons.

* * * * *